(12) United States Patent
Lin et al.

(10) Patent No.: US 11,957,851 B2
(45) Date of Patent: Apr. 16, 2024

(54) CATHETER FOR GUIDING BODY FLUID

(71) Applicant: Flat Medical Inc., Tortola (VG)

(72) Inventors: Li-Yu Lin, New Taipei (TW); Wen-fu Luo, Taipei (TW)

(73) Assignee: Flat Medical Inc., Tortola (VG)

( * ) Notice: Subject to any disclaimer, the term of this patent is extended or adjusted under 35 U.S.C. 154(b) by 438 days.

(21) Appl. No.: 16/603,888

(22) PCT Filed: Apr. 10, 2018

(86) PCT No.: PCT/US2018/026777
§ 371 (c)(1),
(2) Date: Oct. 9, 2019

(87) PCT Pub. No.: WO2018/191193
PCT Pub. Date: Oct. 18, 2018

(65) Prior Publication Data
US 2020/0114125 A1 Apr. 16, 2020

Related U.S. Application Data

(60) Provisional application No. 62/483,483, filed on Apr. 10, 2017.

(51) Int. Cl.
*A61M 25/00* (2006.01)
*A61M 25/04* (2006.01)
(Continued)

(52) U.S. Cl.
CPC ........ *A61M 25/0662* (2013.01); *A61M 25/04* (2013.01); *A61M 27/00* (2013.01);
(Continued)

(58) Field of Classification Search
CPC .......... A61M 25/0074; A61M 25/0075; A61M 2025/0076; A61M 2025/0078
See application file for complete search history.

(56) References Cited

U.S. PATENT DOCUMENTS 3,503,400 A * 3/1970 Osthagen .............. A61F 2/0022
604/249
3,692,029 A * 9/1972 Adair .................... A61M 25/06
604/105

(Continued)

OTHER PUBLICATIONS

International Search Report and Written Opinion of the International Searching Authority issued in PCT/US2018/026777, dated Jul. 3, 2018; ISA/US.

*Primary Examiner* — William R Carpenter
(74) *Attorney, Agent, or Firm* — Harness, Dickey & Pierce, P.L.C.

(57) ABSTRACT

A catheter for guiding a body fluid of a subject includes an elongated body, an adjusting mechanism, and a valve mechanism. Moreover, the elongated body further includes a first portion, a second portion and a flexible portion between the first and the second portions. The second portion includes a passageway for the body liquid. The valve mechanism closes to the inlet of the passageway. Furthermore, the flexible portion expands when the adjusting mechanism is in a first state to prevent the catheter from being removed from the subject, and the flexible portion retracts when the adjusting mechanism alters to a second state to allow the catheter to be removed from or inserted into the subject. Hence, the body fluid is directed to enter the passageway via the inlet and exit via the outlet when the adjusting mechanism is not in the second state.

16 Claims, 10 Drawing Sheets

(51) Int. Cl.
*A61M 25/06* (2006.01)
*A61M 27/00* (2006.01)

(52) U.S. Cl.
CPC . *A61M 25/0017* (2013.01); *A61M 2202/0496* (2013.01); *A61M 2205/04* (2013.01)

(56) References Cited

U.S. PATENT DOCUMENTS

| | | | | |
|---|---|---|---|---|
| 3,713,447 | A * | 1/1973 | Adair | A61M 25/06 |
| | | | | 604/105 |
| 3,812,841 | A * | 5/1974 | Isaacson | A61F 2/0022 |
| | | | | 604/249 |
| 5,483,976 | A * | 1/1996 | McLaughlin | A61M 31/00 |
| | | | | 128/885 |
| 10,675,435 | B2 * | 6/2020 | Herrera | A61M 27/002 |
| 2001/0034470 | A1 | 10/2001 | Whalen et al. | |
| 2009/0024087 | A1 | 1/2009 | Kennedy, II et al. | |
| 2010/0076402 | A1 | 3/2010 | Mazzone et al. | |
| 2010/0331825 | A1 * | 12/2010 | Hakky | A61M 25/0905 |
| | | | | 604/544 |
| 2016/0271377 | A1 * | 9/2016 | Pendleton | A61M 25/04 |

* cited by examiner

CATHETER FOR GUIDING BODY FLUID

CROSS REFERENCE TO RELATED APPLICATION

The present application claims priority to U.S. Provisional Application Ser. No. 62/483,483 filed on Apr. 10, 2017, which is incorporated by reference in its entirety.

FIELD

The present disclosure relates to a medical catheter and more particularly to a medical catheter for guiding body fluid such as urine.

BACKGROUND

Urinary retention is the inability to empty the bladder. It is a common and serious problem resulting from numerous reasons, one of which is aging. Moreover, urinary retention in males often is caused by obstruction of the urethra, nerve problem, improper medication or weakened bladder muscle.

An obstruction occurs when urine is blocked from flowing freely through the urinary track. The common causes of obstructive urinary retention include: benign prostate hyperplasia (BPH), urethral stricture, and kidney or bladder stones. As for non-obstructive ones (e.g., weakened bladder muscle, improper medication or nerve problem), signals between the brain and the bladder are interfered. The common causes of non-obstructive urinary retention include stroke, pelvic injury, trauma, nerve disease, impaired muscle, nerve dysfunction due to medication, anesthesia, and accidents that injure the brain or spinal cord.

According to studies, the overall incidence rate of urinary retention is 4.5 to 6.8 per 1,000 men between the age of 40 to 83. Specifically, for men in their 70s, the overall incidence rate increases to 100 per 1,000 men. The incidence rate of acute urinary retention increases up to 300 per 1,000 men in their 80s. Patients with acute or chronic urinary retention develop different symptoms. Those with acute urinary retention may experience inability to urinate, pain or urgent need to urinate, severe pain or discomfort in the lower abdomen, and bloating of the lower abdomen. Immediate medical attention is needed.

Treatments for urinary retention include catheterization, urethral dilation, urethral stent, prostate-specific medicine, and surgery. However, such treatments are not always suitable for all patients. For example, neurogenic urinary retention patients may only have the option of catheterization. Present catheterization techniques include the Foley catheter (urethral catheter), suprapubic drainage tube, or intermittent catheterization.

The Foley catheter (i.e., the indwelling catheter) includes two separated channels or lumens running down its length. One of the channels has openings at both ends and is responsible for draining the urine into a collection bag. The other channel has a valve at its outer end and a balloon at its inner tip. When the balloon is placed inside the bladder, it is filled with sterile water so as to serve as an anchor to prevent the catheter from slipping out. However, the Foley catheter has several disadvantages, including encrustation, blockage, structural damage to urethra and bladder, facilitate development of bladder or kidney stones, and infection (e.g., urinary tract infections (UTI), kidney infection, and blood infection).

Comparing to the Foley catheter, suprapubic catheter may result in a lower rate of urethral injury and stricture. However, it still causes upper tract damage, vesicoureteral reflux, renal or bladder calculi, and urinary tract infections.

Intermittent catheterization is the insertion and removal of a catheter several times a day to empty the bladder, and it reduces the need of the long-term indwelling catheter. However, intermittent catheterization involves patient acceptance and manual handling. It requires up to 20 minutes to complete the entire procedure, i.e., insertion or the removal of the catheter, each time. It is inconvenient for patients and often creates embarrassment when, e.g., operating the procedure away from home. Additionally, several reports show that the complications of applying intermittent catheterization with spinal cord injury patients include epididymitis (about 28% incidence rate), urethritis (about 18% incidence rate), and prostatitis (about 33% incidence rate).

As discussed, conventional treatments/devices have a relatively high infection rate and are also inconvenient for patients and caregivers. As a result, urinary retention patients may experience discomfort and are less motivated to participate in social activities, resulting in deteriorated life quality.

To overcome issues above, U.S. Pat. No. 7,547,291 disclosed a device (i.e., the urethral prosthesis) to relieve urinary retention. The device includes a first and a second tubular elements with an interposed bridge segment. The first tubular element further includes a drainage hole, a channel for fluid flow, and an inflatable balloon for maintaining the position of the urethral prosthesis. Further, the device includes a valve disposed in the second tubular element to control urine flow. The device does not require an external tube or collection bag. Furthermore, the patient can actively control the device to empty his/her bladder. However, the balloon is deposited near the tubular tip and thus may result in incomplete drain of the urine. The residual urine in the bladder, after prolonged period, may cause irritation and eventually induce bladder infection. Similar design of such devices can be found in U.S. Pat. Nos. 6,835,183, 6,234,956, 9,622,848 and 8,096,986.

U.S. Pat. No. 20160015936 and U.S. Pat. No. 9,011,314 disclosed a urinary flow control system (i.e., the CymActive™ System). The system can be placed and retained in the bladder and the urine tract, and further pass through two sphincters. More specifically, the system utilizes the malecot anchor to retain its position in the bladder. The system further includes a magnetic valve at the distal end, through which the patient can control the opening and closing of the valve by an actuator magnet. The system is self-retaining and allows cyclical bladder to be filled and emptied without an external appliance. The malecot anchor can be further used to enhance drainage. However, the magnetic valve may cause patient discomfort due to its size. Moreover, the patient needs to carry the actuator magnet at all times. Without the actuator magnet, urine accumulation will occur and may lead to pressure increase in the kidneys. This may cause kidney failure or even permanent damage to the kidney. Similar designs of magnetic actuation urethral valve can be found in U.S. Pat. Nos. 6,234,956 and 5,030,199.

U.S. Pat. No. 8,137,337 disclosed an indwelling urinary catheter with a self-retaining mechanism. The self-retaining mechanism of the catheter operates by means of an actuating linkage wire to control the catheter between an "opened state" and a "closed state". Hence, no extra anchoring element is needed to prevent the catheter from being pulled out of the patient accidentally. Moreover, such self-retaining mechanism results in continuous drainage of the bladder, which may lower the chance of urine residue and infection. Although the catheter provides an improved retaining mechanism to facilitate the introduction and removal of the catheter, it still has several defects. For example, in order to provide enough force to maintain the catheter in the opened state, the material of the actuating mechanism needs to be hard, rigid plastic such as PP (polypropylene), PE (polyethylene), PC (polycarbonate), and etc. However, these materials are prone to cause discomfort and pain to patients.

U.S. Pat. No. 6,589,208 disclosed a self-deploying catheter assembly. The primary structure of the catheter assembly includes an anchoring device mounted to a tube. The anchoring device automatically maintains a tubular shape with the ends spaced apart during insertion into a body cavity, and converts into a mushroom shape when the catheter is fully inserted and the tube is slightly withdrawn from the body cavity. Also, the catheter includes a suture, which is designed to be releasable from the distal end of the anchor so as to facilitate the tubular shape. However, the inlet of the catheter is at the end of the anchor, which is not at the bottom of the bladder when the catheter is disposed. Consequently, urine in the bladder may not be completely drained, causing irritation and infection of the bladder. Furthermore, an operator is required to manually convert the catheter to a mushroom shape. Specifically, the operator needs to use a wire to control whether the anchor is converted to the mushroom shape. In other words, an additional element is needed for the catheter to maintain the anchor at the mushroom shape. Such additional element adds more difficulty to the manufacturing process and lowers the easiness of operability. Essentially, the foregoing is materially the same as a Lotus catheter and thus possesses identical disadvantages.

The object of the present disclosure is to provide a device that can properly drain the bladder and is easy to operate. Therefore, the device can not only reduce the possibility of complications, but also make it easier to install or remove.

SUMMARY

The present disclosure provides a catheter for guiding the body fluid of a subject. The catheter includes an elongated body having a proximal tip and a distal tip and an adjusting mechanism with two opposite ends. In one aspect, the catheter further includes a first portion, a second portion and a flexible portion between the first and the second portions. The second portion includes a circumferential wall defining a passageway for the body liquid, and the passageway further includes an inlet and an outlet. In another aspect, the first end of the adjusting mechanism connects the first portion of the catheter, and the second end of the adjusting mechanism engages the second portion of the catheter proximate to the inlet of the passageway. The adjusting mechanism is adapted to alter between different states. Furthermore, the flexible portion of the catheter expands to anchor the catheter inside the subject when the adjusting mechanism is in a first state, and the adjusting mechanism alters to a second state when the flexible portion retracts to allow insertion or withdrawal of the catheter to/from the subject. Also, the body fluid is directed to enter the passageway via the inlet of the second portion and exit via the outlet of the second portion.

In some embodiments, the first portion of the elongated body further includes a compartment, and the adjusting mechanism further includes a biasing element close to the first end. Furthermore, the biasing element is received within the compartment.

In some embodiments, the biasing element is compressed in the second state.

In some embodiments, the adjusting mechanism is stretched in the second state.

In some embodiments, the second end of the adjusting mechanism does not block the passageway.

In some embodiments, the catheter further includes an extraction wire connected to the second portion, said extraction wire is adapted to extend outside the subject such that it can be easily pulled to withdraw the catheter.

In some embodiments, a length of the second portion is about 4-6 centimeters.

In some embodiments, the second end of the adjusting mechanism includes a first valve mechanism proximate to the inlet of the passageway, the body fluid can enter the passageway via the inlet when the first valve mechanism is opened and the body fluid is blocked from entering the passageway when the first valve mechanism is closed.

In some embodiments, the first portion of the elongated body further includes a compartment, and the adjusting mechanism further includes a biasing element near the first end. Moreover, the biasing element is received within the compartment.

In some embodiments, a length of the second portion is about 7-10 centimeters.

In some embodiments, the adjusting mechanism includes a controlling wire configured to open or close the first valve mechanism.

In some embodiments, the flexible portion further expands such that the flexible portion and the first portion are more securely anchored within the subject when the controlling wire is pulled to open the first valve mechanism.

In some embodiments, the catheter further includes a locking module and a second valve mechanism. Moreover, the locking module received within the first portion of the catheter and engages with the adjusting mechanism. The second valve mechanism is at a distal end of the controlling wire and it controls the body fluid from leaving the passageway via the outlet. Furthermore, the locking module controls the opening and closing of the inlet when the adjusting mechanism is not in the second state.

In some embodiments, a length of the second portion is about 15-20 centimeters.

In some embodiments, the outlet of the passageway is outside the subject.

In some embodiments, the flexible portion comprises at least two arms.

In some embodiments, a material of the catheter comprises polyvinyl chloride (PVC), silicon, thermoplastic polyurethane (TPU), thermo-plastic-rubber (TPR) or any combination thereof.

In some embodiments, only the first portion and the flexible portion are placed in a cavity of the subject when the catheter is not in the second state.

In some embodiments, the cavity is defined by a bladder.

The present disclosure also provides a catheter for guiding a body fluid of a subject. The catheter includes an elongated body having a proximal tip and a distal tip, an adjusting mechanism with a first end and an opposite second end, and a valve mechanism at the second end of the adjusting mechanism. In one aspect, elongated body further includes a first portion, a second portion and a flexible portion between the first and the second portions. The portion includes a circumferential wall defining a passageway for the body liquid. The passageway further includes an inlet and an outlet. In another aspect, the first end of the adjusting mechanism engages the first portion of the catheter. The valve mechanism engages the second portion proximate to the inlet of the passageway. Furthermore, the body fluid can enter the passage via the inlet when the valve mechanism is opened and the body fluid is blocked from entering the passageway when the valve mechanism is closed. Specifically, the adjusting mechanism is in a first state when the flexible portion expands to anchor the catheter inside the subject, and the adjusting mechanism alters to a second state when the flexible portion retracts to allow the insertion or withdrawal of the catheter to/from the subject. Hence, the body fluid is directed to enter the passageway via the inlet of the second portion and exit via the outlet of the second portion.

BRIEF DESCRIPTION OF THE DRAWINGS

One or more embodiments are illustrated by way of example, and not by limitation, in the figures of the accompanying drawings, wherein elements are having the same reference numeral designations represent like elements throughout. The drawings are not to scale, unless otherwise disclosed.

FIG. 3 include three sectional views (FIG. 3A to 3C) of a catheter with a valve mechanism for controlling the flow of the body fluid in accordance with some embodiments of the present disclosure.

FIG. 4 include three sectional views (FIG. 4A to 4C) of another catheter with different adjusting mechanism and a valve mechanism for controlling the flow of the body fluid in accordance with some embodiments of the present disclosure.

Figure 1:
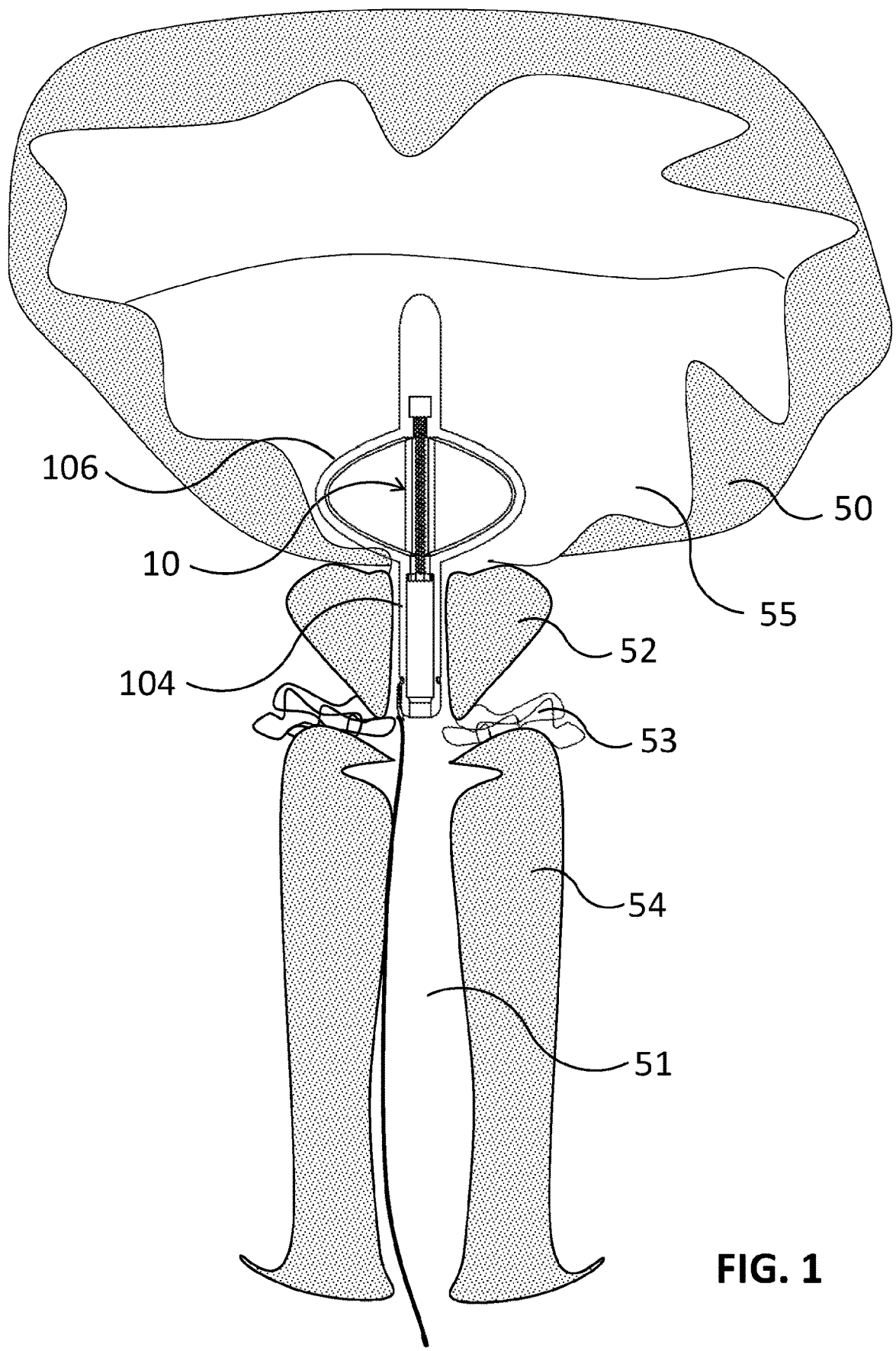
FIG. 1 is a schematic view of a catheter without a valve mechanism for guiding a body fluid, placed at a correct position in a bladder in accordance with some embodiments of the present disclosure.

The drawings are only schematic and are non-limiting. In the drawings, the size of some of the elements may be exaggerated and not drawn on scale for illustrative purposes.

The dimensions and the relative dimensions do not necessarily correspond to actual reductions to practice of the invention. Any reference signs in the claims shall not be construed as limiting the scope. Like reference symbols in the various drawings indicate like elements.

DETAILED DESCRIPTION OF THE DISCLOSURE

The making and using of the embodiments of the disclosure are discussed in detail below. It should be appreciated, however, that the embodiments provide many applicable inventive concepts that can be embodied in a wide variety of specific contexts. The specific embodiments discussed are merely illustrative of specific ways to make and use the embodiments, and do not limit the scope of the disclosure.

Throughout the various views and illustrative embodiments, like reference numerals are used to designate like elements. Reference will now be made in detail to exemplary embodiments illustrated in the accompanying drawings. Wherever possible, the same reference numbers are used in the drawings and the description to refer to the same or like parts. In the drawings, the shape and thickness may be exaggerated for clarity and convenience. This description will be directed in particular to elements forming part of, or cooperating more directly with, an apparatus in accordance with the present disclosure. It is to be understood that elements not specifically shown or described may take various forms. Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. It should be appreciated that the following figures are not drawn to scale; rather, these figures are merely intended for illustration.

Definition

It will be understood that when an element is referred to as being "on" another element, it can be directly on the other element or intervening elements may be present. In contrast, when an element is referred to as being "directly on" another element, there are no intervening elements present.

It will be understood that singular forms "a", "an" and "the" are intended to include the plural forms as well, unless the context clearly indicates otherwise.

The term "about," as used herein, when referring to a measurable value such as an amount, a temporal duration, and the like, is meant to encompass variations of ±5% and more preferably ±1% from the specified value, as such variations are appropriate to perform the disclosed methods.

Unless otherwise defined, all terms (including technical and scientific terms) used herein have the same meaning as commonly understood by one of ordinary skill in the art to which this disclosure belongs. It will be further understood that terms; such as those defined in commonly used dictionaries, should be interpreted as having a meaning that is consistent with their meaning in the context of the relevant art and the present disclosure, and will not be interpreted in an idealized or overly formal sense unless expressly so defined herein.

DETAILED DESCRIPTION

The present disclosure provides a catheter, which can be placed inside the body mass of a patient to help drain urine. FIG. 1 is a schematic view of a catheter 10 (i.e., a frame) without a valve mechanism for guiding a body fluid (e.g., urine 55), placed at a correct position in a bladder 50. As the figure shows that only a second portion 104 of the catheter 10 passes through a prostate 52 (i.e., only the second portion of the catheter 10 is deposited within the urethra 51) when the catheter 10 is correctly placed in the body cavity (e.g., bladder 50) of a subject. Further, a flexible portion 106 of the catheter 10 is expanded and acts as an anchor to maintain the catheter 10 in a correct position when the catheter 10 is in a normal state. Hence, the urine 55 inside the bladder 10 is drained out through the second portion 104 of the catheter 10.

Figure 2A:
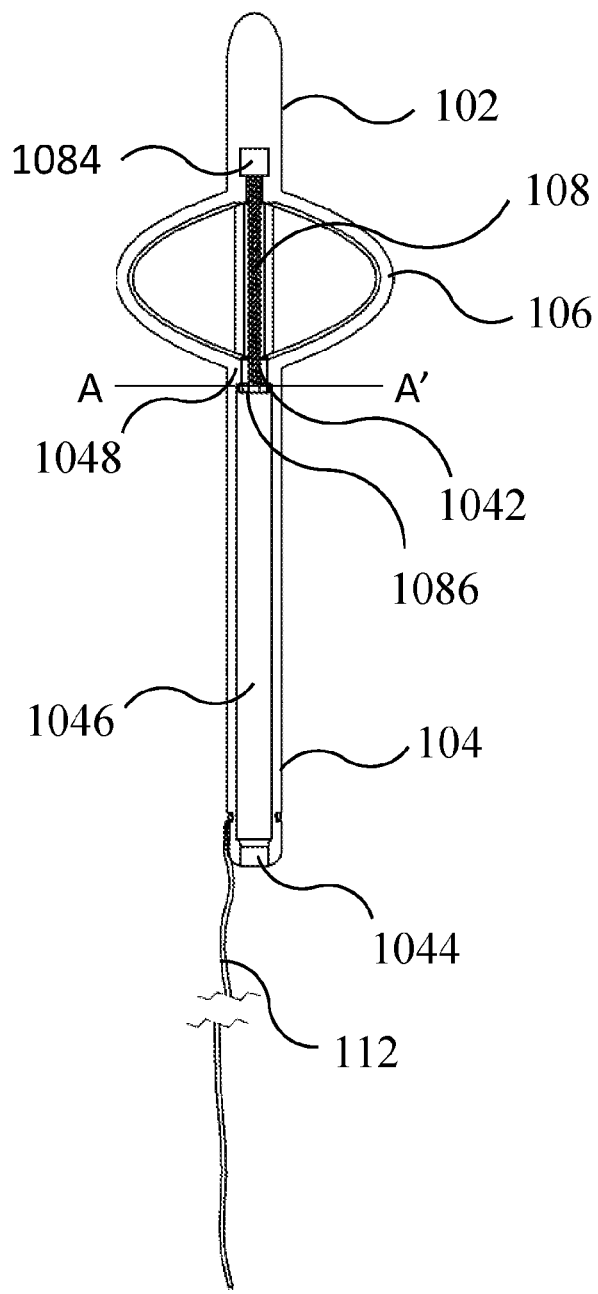
FIG. 2A discloses the catheter is deformed when an adjusting mechanism is in a first state, and FIG. 2C discloses the catheter is in a tubular form when the adjusting mechanism is in a second state.
Figure 2B:
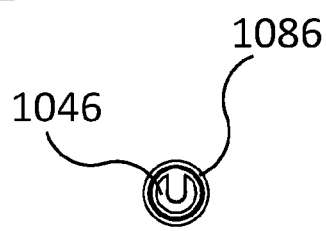
FIG. 2B is a cross section view in the direction of line A-A'.
Figure 2C:
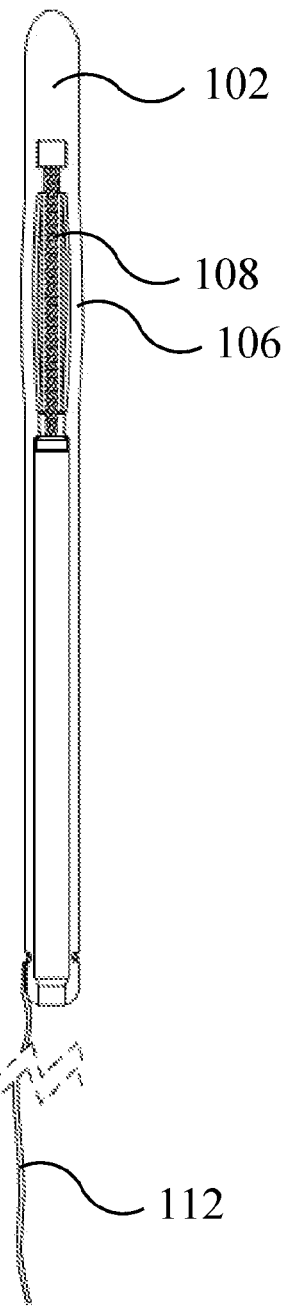
FIG. 2 include three sectional views (FIG. 2A to 2C) of the catheter without the valve mechanism for guiding a body fluid in accordance with some embodiments of the present disclosure.

FIG. 2 include three sectional views (FIG. 2A to 2C) of the catheter 10 without the valve mechanism for guiding a body fluid. According to FIG. 2A, the catheter 10 includes an elongated body having a proximal tip and a distal tip and an adjusting mechanism 108 with two opposite ends (i.e., a first end 1084 and a second end 1086). Furthermore, the elongated body of the catheter 10 includes a first portion 102, a second portion 104 and a flexible portion 106 situated between the first and the second portions. The second portion 104 includes a circumferential wall defining a passageway 1046 for the body fluid to flow, and the passageway 1046 further includes an inlet 1042 and an outlet 1044. In some embodiments, the second portion 104 may further include an extraction wire 112 connecting to the second portion 104 near the outlet 1044 for an operator to remove the catheter 10. Furthermore, the inlet 1042 of the second portion 104 further includes a sheath 1048. In another aspect, the first end 1084 of the adjusting mechanism 108 is affixed to the first portion 102 of the catheter 10, and the second end 1086 of the adjusting mechanism 108 engages the sheath 1048 of the second portion 104 near the inlet 1042 of the passageway 1046. The adjusting mechanism 108 can be made of a biasing element (e.g., a spring) or an elastic element (e.g., an elastic wire). The length of the adjusting mechanism 108 changes when it is being compressed or stretched from its resting (i.e., equilibrium) position. When the adjusting mechanism 108 is in its resting, equilibrium state, i.e., when no stretching or compressing force is applied and the adjusting mechanism 108 is at its default length, the flexible portion 106 is expanded, allowing the catheter to anchor inside the body cavity. When the adjusting mechanism 108 is stretched (which causes the adjusting mechanism 108 to lengthen), the flexible portion 106 will retract to allow the catheter 10 to change to a tubular shape. When the adjusting mechanism 108 is compressed (which causes the adjusting mechanism 108 to shorten), the flexible portion 106 expands further to ensure that the catheter cannot be easily removed from the body cavity. According to the present disclosure, the adjusting mechanism 108 is adapted to alter between different states, i.e., changing in lengths, to correspond to the expansion or retraction of the flexible portion 106.

When the adjusting mechanism 108 is in a resting position (i.e., at its default length), the adjusting mechanism 108 is defined as being in a first state. In the first state, the flexible portion 106 of the catheter 10 is expanded and acts an anchor to maintain the catheter 10 inside the body cavity of the subject. The inlet 1042 of the catheter 10 is at or near the bottom of the body cavity when the catheter 10 is properly inserted, allowing the body fluid inside the body cavity to be drained completely.

FIG. 2B is a cross section view, in the direction of line A-A', of the inlet of the second portion 104 in FIG. 2A. The structure of the second end 1086 of the adjusting mechanism (not shown) is a ring or any similar shape that would not obstruct the body fluid from flowing into the passageway 1046.

FIG. 2C illustrates the catheter 10 in a tubular shape, i.e., when the flexible portion 106 retracts. The adjusting mechanism 108 is stretched and is defined as in a second state when the catheter 10 is in such tubular shape. When an operator attempts to remove the catheter 10, the operator may pull the extraction wire 112 to remove the catheter 10 from the body cavity of the subject. The extraction wire 112 is configured to attach to or near the end of the second portion. When the operator pulls the extraction wire 112 to withdraw the catheter, the muscle surrounding the urethra forces the flexible portion to retract and the adjusting mechanism to stretch, and the catheter 10 becomes tubular. In another words, the flexible portion retracts when the adjusting mechanism alters to a second state to allow the catheter to be removed from the subject.

In another aspect, when an operator attempts to insert the catheter 10 into the body cavity of the subject, the operator wants the flexible portion 106 to retract so the catheter 10 is in a tubular shape for easier insertion. The operator applies a force directly to the flexible portion to make it retracts, thereby stretching the adjusting mechanism 108. When the first portion 102 and the flexible portion 106 of the catheter 10 are inserted into the body cavity, the restoring force of the adjusting mechanism 108 will return it to its resting position and expand the flexible portion 106 accordingly.

It is to be noted that each of the flexible portion element (i.e., the flexible portion alone), when not applied with external force, is in a retracted state. In certain embodiment, the flexible portion is continuously longitudinally extended when not receiving a force. In such situation, the catheter is readily removable from the body cavity because the flexible portion does not provide a blocking function. Consequently, when the catheter is not to be removed from the body cavity (catheter not in the second state), a force is applied through the adjusting mechanism so as to deform the flexible portion. Specifically, the flexible portion becomes in the shape of a cage so as to serve as a blocker, stopping the catheter from being extracted from the body cavity. Further, the flexible portion may include at least two flexible arms, and the preferable arm number is three. The catheter 10 maintains a passage through the prostate of the subject, and the preferred length of the second portion of the catheter 10 is about 4-6 centimeters.

The present disclosure also provides another catheter for draining the body fluid where the operator of such catheter can control whether the urine flows out of the subject.

Figure 3A:
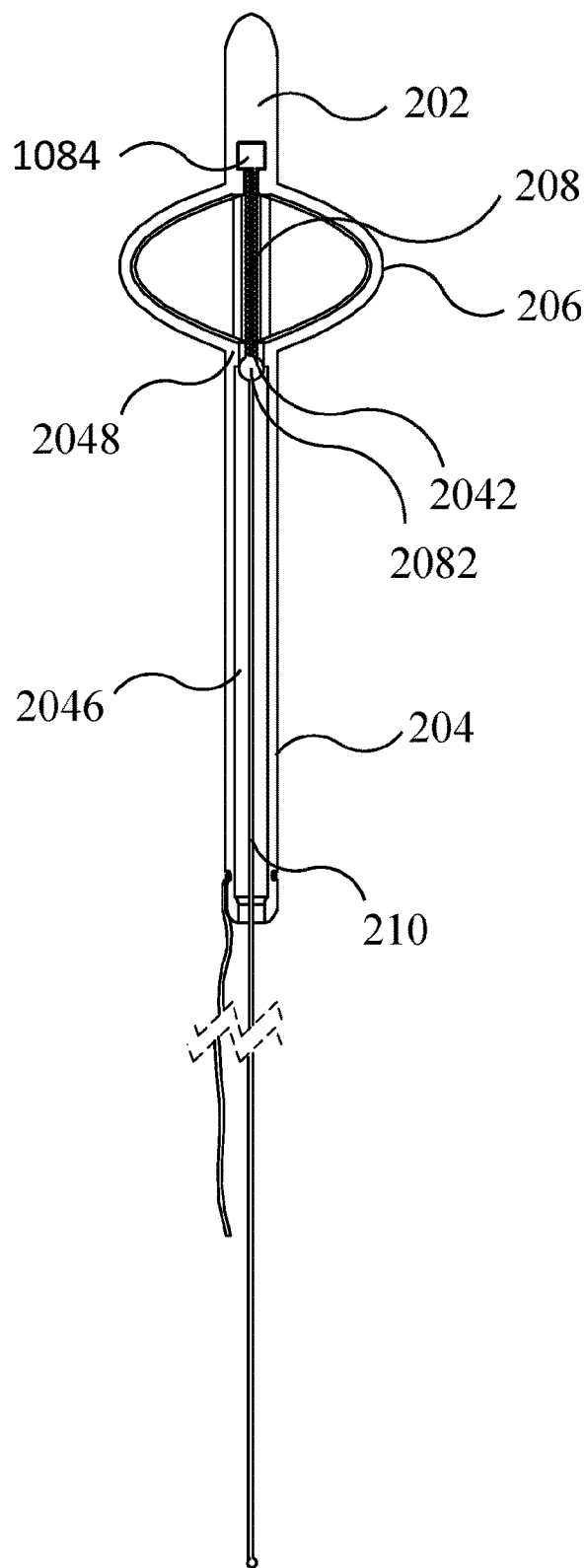
FIG. 3A discloses the catheter is deformed and the valve mechanism is close when an adjusting mechanism is in a first state.

FIG. 3A discloses a catheter 20 with a first valve mechanism 2082 that is closed when an adjusting mechanism 208 is in a resting position (i.e., the first state). As the FIG. 3A shows, the catheter 20 has a first portion 202, a second portion 204, a flexible portion 206 and an adjusting mechanism 208, and the second portion 204 further includes an inlet 2042 and outlet 2044 in the two opposite ends, a sheath 2048 close to the inlet 2042, and a passageway 2046. The catheter 20 further includes the first valve mechanism 2082 at the second end of the adjusting mechanism 208, and a controlling wire 210 connecting to the first valve mechanism 2082 that extends outside the subject's body. The first valve mechanism 2082 is slidably received within the passageway 2046 and detachably engaged with the sheath 2048. As described previously, after the operator inserts the tubular catheter 20 into the body cavity, the restoring force of the adjusting mechanism 208 induces the flexible portion 206 to expand, thereby anchoring the catheter 20 properly inside the cavity. FIG. 3A shows the catheter 20 with flexible portion 206 (e.g., three flexible arms) expanded, and the adjusting mechanism 208 in the first state. Further, the first valve mechanism 2082 (e.g., the globe valve) is engaged with the sheath 2048 and block the inlet 2042 to keep out the body fluid from flowing into the passageway 2046. In other words, the restoring force of the adjusting mechanism 208 helps the first valve mechanism 2082 to more securely engage with the sheath 2048 to block the inlet 2042.

Figure 3B:
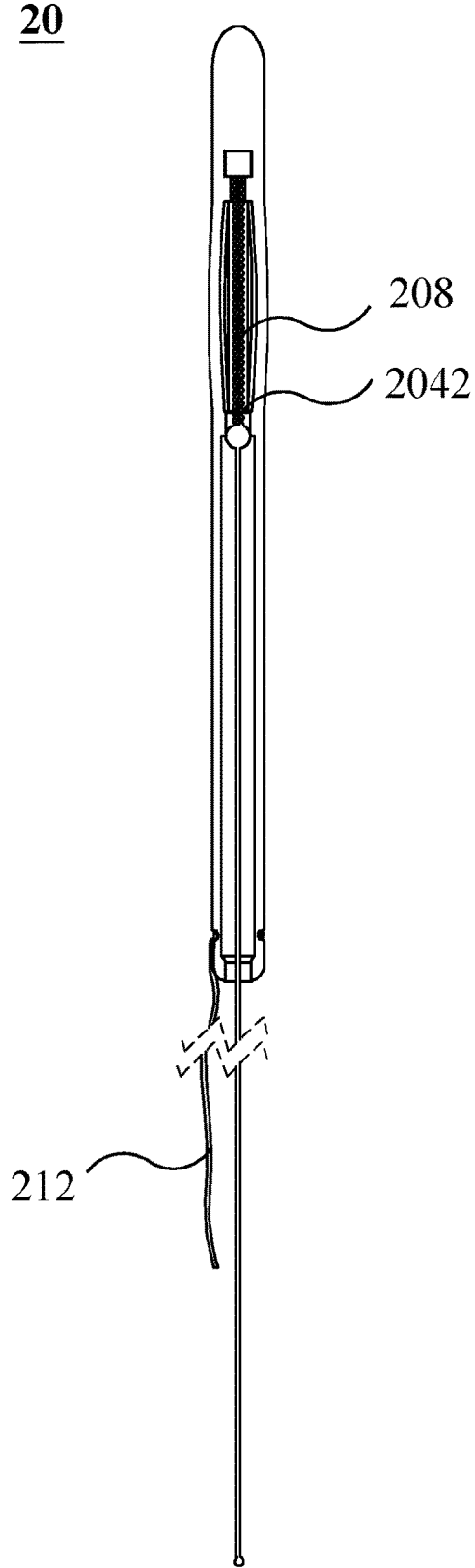
FIG. 3B discloses the catheter is in a tubular form when the adjusting mechanism is in a second state.

FIG. 3B shows the catheter 20 in a tubular form when the adjusting mechanism 208 is in a second state. As previously described, the operator can retract the flexible arms of the flexible portion 206 to make the catheter 20 tubular, allowing easier insertion or withdrawal in/from the body cavity. In some embodiments, the catheter 20 may further includes an extraction wire 212 that can help withdrawing the catheter 20.

Figure 3C:
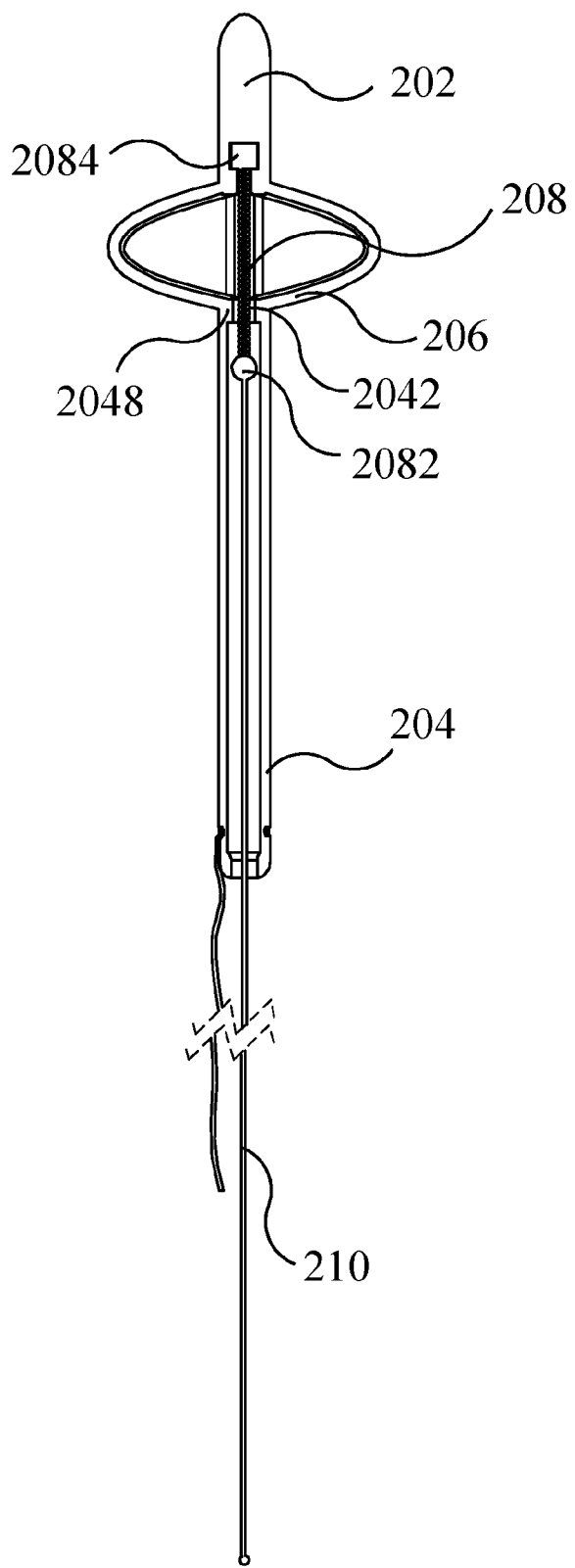
FIG. 3C discloses the catheter is deformed and further the valve mechanism is also open when an adjusting mechanism is not in the first and the second state.

FIG. 3C discloses the catheter 20 with the first valve mechanism 2082 opened when the adjusting mechanism 208 is not in the first and the second state. Thus, the adjustment mechanism is in a third state. When the operator needs to drain the body fluid (e.g., urine), the operator can simply pull the controlling wire 210 to disengage the first valve mechanism 2082 from the sheath 2048 (i.e., let the inlet 2042 open). Specifically, when the pulling force that the operator applies to the controlling wire 210 is greater than the restoring force of the adjusting mechanism 208, the first valve mechanism 2082 moves away from the sheath 2048.

Furthermore, if the operator continues to pull the controlling wire 210 after the adjusting mechanism is stretched to its maximal length, the pulling force of the controlling wire 210 will cause the position of the adjusting mechanism 208 relatives to the catheter 20 to shift. Since the first end 2084 is affixed to the first portion 202, the shifting of the adjusting mechanism 208 will shorten the distance between the first end 2084 and the inlet 2042. Accordingly, the flexible portion 206 expands further, and the diameter of the cage formed by the flexible arms increases more. Such configuration may better anchor the first portion 202 and the three flexible arms (i.e., the flexible portion 206) within the body cavity. If the operator wants to close the inlet 2042, the operator simply releases the controlling wire 210, and the adjusting mechanism 208 will restore the catheter 20 back to the state as FIG. 3A shows.

In one aspect, the number of the flexible arms is at least two, and the preferred number is three. In another aspect, the adjusting mechanism 208 can be made of a spring or an elastic wire. Furthermore, the length of the second portion 204 of the catheter 20 is about 7-10 centimeters.

Figure 4A:
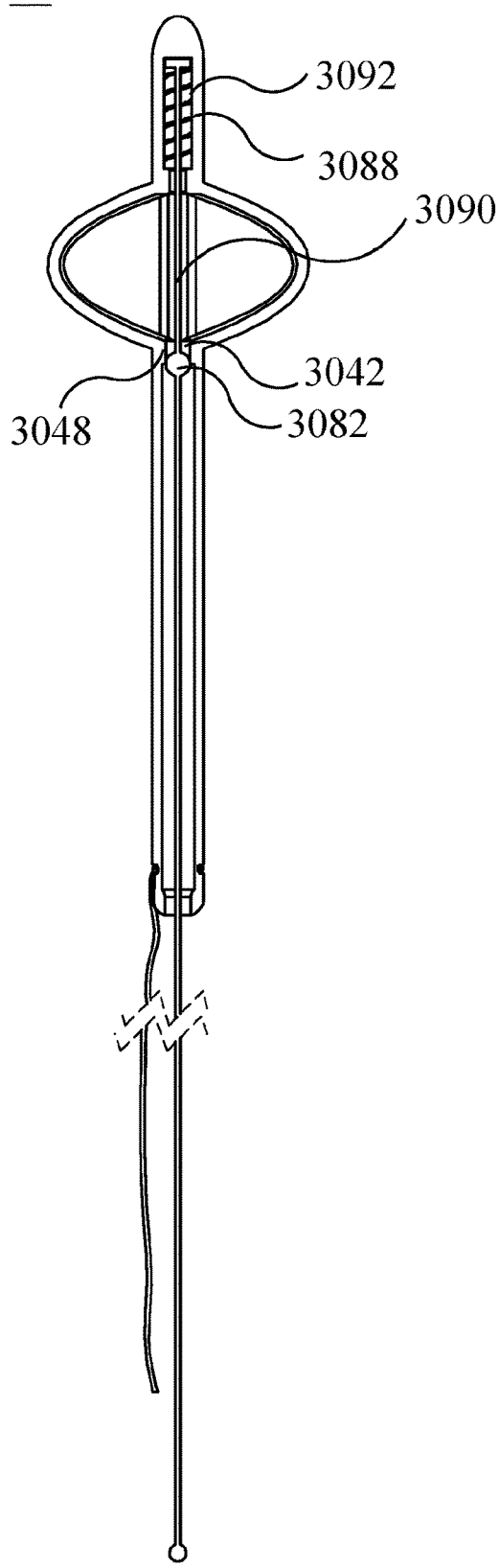
FIG. 4A discloses the catheter is deformed and the valve mechanism is close when an adjusting mechanism is in a first state.

FIG. 4 further disclose another catheter 30 with the first valve mechanism 3082. The different between the catheter 30 and the previous catheters is the structure of the adjusting mechanism. FIG. 4A illustrates the catheter 30 with the first valve mechanism 3082 closed when the adjusting mechanism is in a first state. As FIG. 4A shows, the adjusting mechanism includes a biasing element 3088 (e.g., a spring) and a connecting wire 3090. Further, the first portion 302 of the catheter 30 has a compartment 3092 for receiving the biasing element 3088 and a portion of the connecting wire 3090. When the biasing element 3088 has a maximal length inside the compartment 3092, it is defined as in a first state (i.e., a default state), and the biasing element 3088 induces the first valve mechanism 3082 to engage with the sheath 3048 to block the inlet 3042.

Figure 4B:
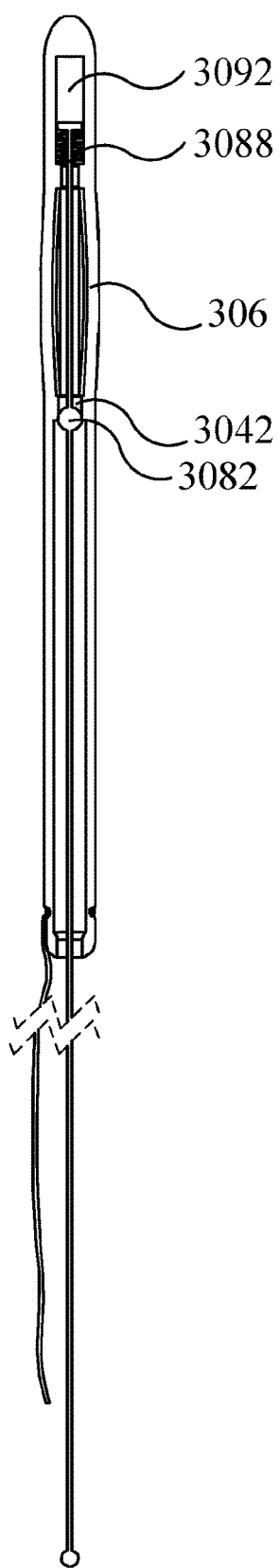
FIG. 4B discloses the catheter is in a tubular form when the adjusting mechanism is in a second state.

FIG. 4B discloses the catheter 30 in tubular form when the adjusting mechanism is in a second state. The operator retracts the flexible portion 306 (e.g., the flexible arms) for easy insertion or withdrawal of the catheter 30. When the catheter 30 is in the tubular shape, the biasing element 3088 inside the compartment 3092 is compressing to a minimal length and is defined as in a second state. The compressing biasing element 3088 is capable of inducing the first valve mechanism 3082 to securely block the inlet 3042.

Figure 4C:
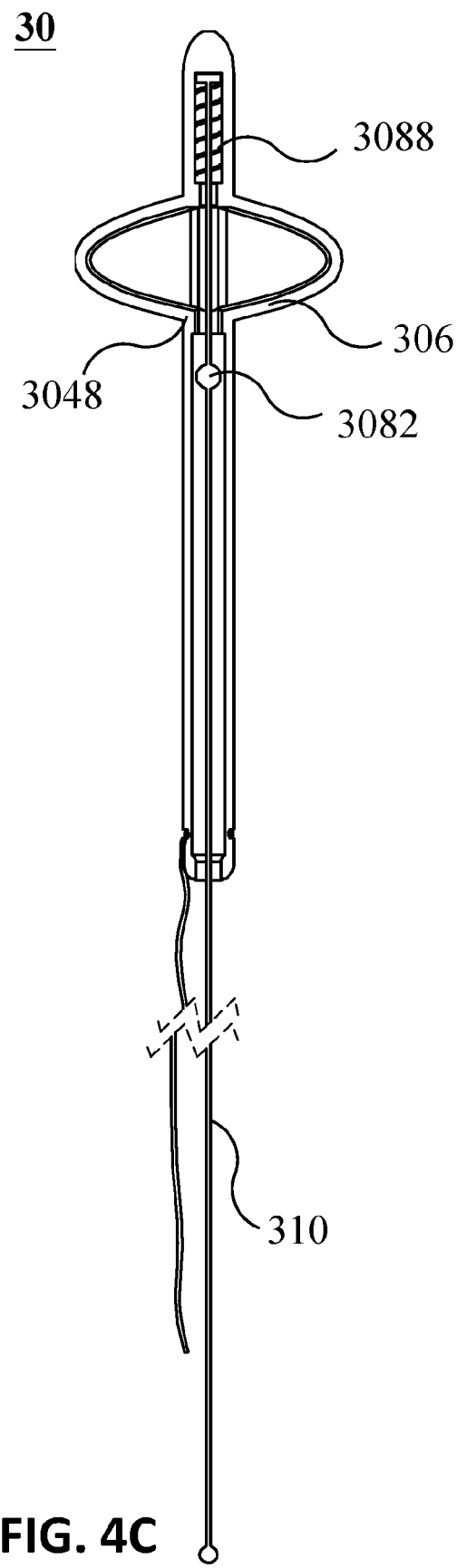
FIG. 4C discloses the catheter is deformed and further the valve mechanism is also open when an adjusting mechanism is not in the first and the second state.

FIG. 4C discloses the catheter 30 with the first valve mechanism 3082 opened when the biasing element 3088 is not in the first and the second state. When the operator needs to open the first valve mechanism 3082 to drain the body fluid, the operator simply tugs the controlling wire 310 to disengage the first valve mechanism 3082 from the sheath 3048. Simultaneously, the diameter of the cage formed by the flexible portion 306 lengthens and provides better anchoring ability.

Figure 5:
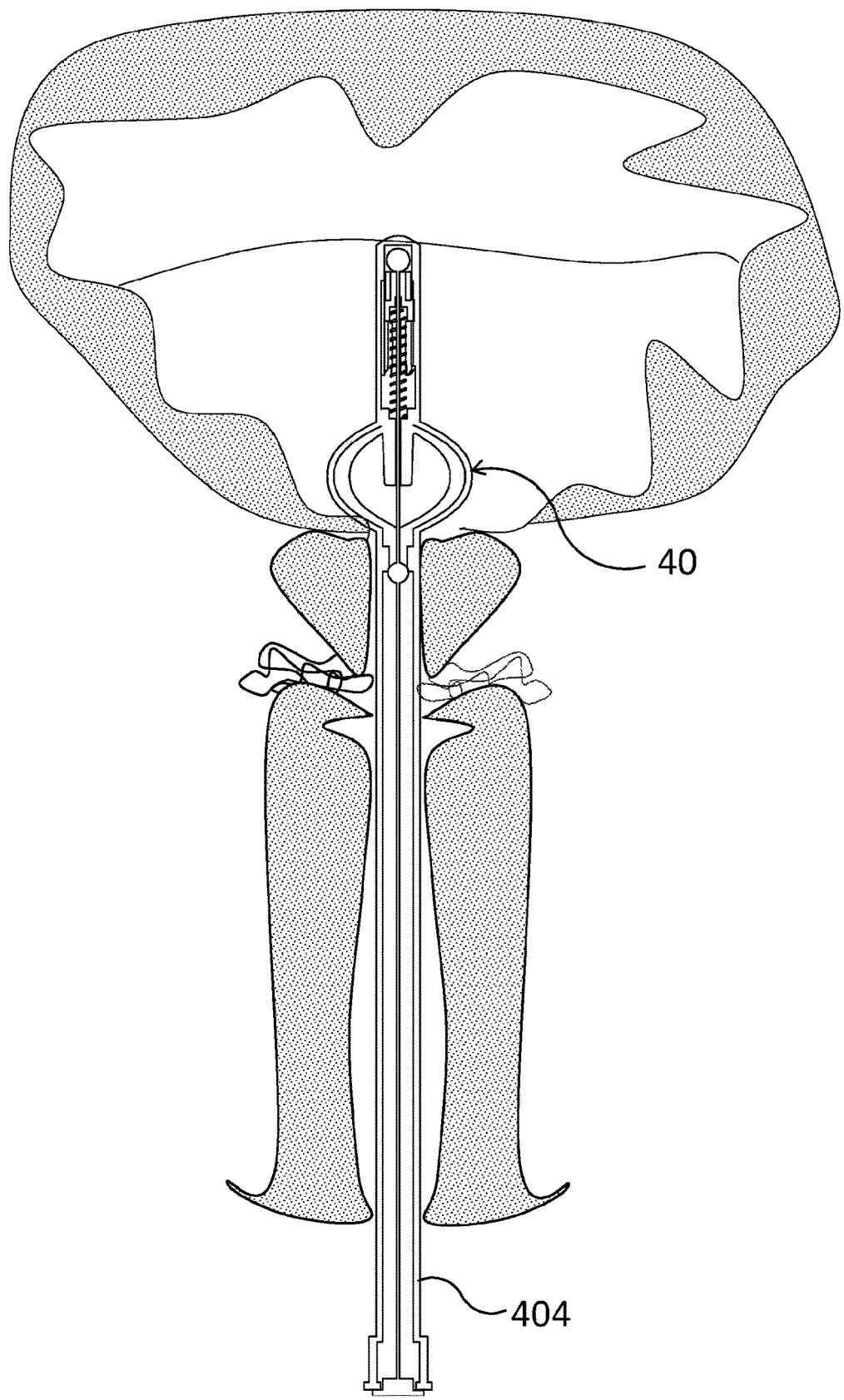
FIG. 5 is a schematic view that a catheter with a locking module and two valve mechanisms for controlling the flow of the body fluid is placed at a correct position in a bladder and further a portion of the catheter extends outside the body mass in accordance with some embodiments of the present disclosure.
Figure 6A:
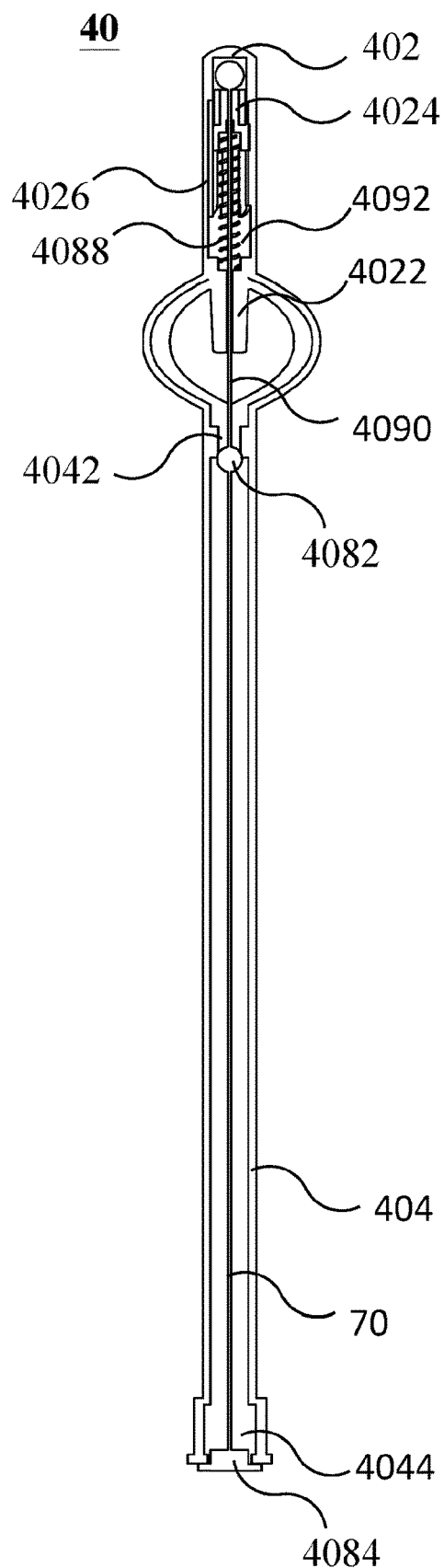
FIG. 6 include four sectional views (FIG. 6A to 6D) of the catheter with a locking module and two valve mechanisms for controlling the flow of the body fluid in accordance with some embodiments of the present disclosure.

The present disclosure further provides an unembedded catheter. As FIG. 5 shows, the unembedded catheter 40 has an elongated second portion 404, and therefore a section of the second portion 404 extends outside the subject's body when it is inserted. FIG. 6 disclose the detailed structure of the unembedded catheter 40. As FIG. 6A shows, the catheter 40 includes not only the elongated second portion 404 but also a locking module inside the compartment 4092 of the first portion 402, a second valve mechanism 4084 at the end of a connecting wire 4090 away from the first valve mechanism 4082, and a cylindrical block 4022 protruding from the end of the first portion 402 that closes to the inlet 4042. Furthermore, the locking module includes multiple teeth 4026 on the inner wall of the first portion 402 and a locking gear 4024 that connects to the end of the connecting wire 4090 and is slidably received within the compartment 4092. Moreover, the multiple teeth 2046 are capable of maintaining the locking gear 4024 in multiple positions (e.g., two different positions) for controlling the first valve mechanism 4082 and the second valve mechanism 4084. As FIG. 6A shows, when the catheter 40 is in a normal state, the biasing element 4088 is in a first state with a maximal length, and the locking gear 4024 is in a first position relative to the teeth 4026. When the locking gear 4024 is in the first position, the catheter 40 is properly inserted and position thereof is maintained because the flexible arms are expanded by the biasing element 4088. Further, the first valve mechanism 4082 blocks the inlet 4042 of the second portion 404, and the second valve mechanism 4084 blocks the outlet 4044 of the second portion 404. In other words, the body fluid cannot flow in or out of the catheter 40. It is worth to note that the locking gear 4024 is secured by the teeth 4026 when the locking gear 4024 is in the first position.

Figure 6B:
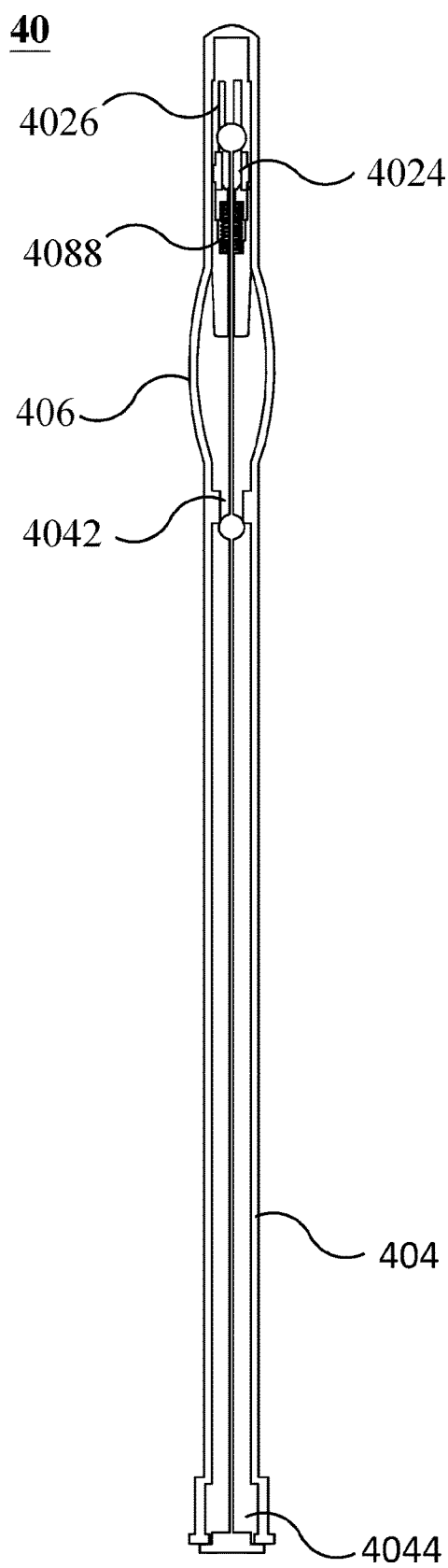

As FIG. 6B shows, the operator retracts the flexible arms to make the catheter 40 tubular for easy insertion or withdrawal. Here, the biasing element 4088 is in the second state and is compressed, and the locking gear 4024 moves to a second position relative to the teeth 4026. Moreover, the inlet 4042 and the outlet 4044 of the second portion 404 are closed, and the locking gear 4024 is secured by the teeth 4026 in the second position. In other words, the catheter 40 will maintain in the tubular shape when the operator moves the locking gear 4024 to the second position. It is important to note that the catheter 40 only becomes readily removable from the subject's body when the locking gear 4024 is at the second position. The locking gear 4024 serves to prevent the catheter 40 from accidentally becoming tubular and readily removable from the subject's body. Here, the strength of the biasing element 4088 in this embodiment is specifically configured such that the flexible portion cannot be retracted easily, as shown in FIG. 6A. In particular, the biasing element 4088 is designed to sustain a substantial amount of away-pulling force applied to the second portion 404. Such sustention serves to maintain the flexible portion 406 in a caged shape, without being deformed by the counterforce from the muscle surrounding the urethra. Only when the locking gear 4024 is at the second position will the catheter 40 become tubular. In sum, the locking module (i.e., the teeth 4026 and the locking gear 4024) serves to switch the catheter 40 between different shapes/states and to prevent users from accidentally remove the catheter in an undesirable manner or when unwanted.

Figure 6C:
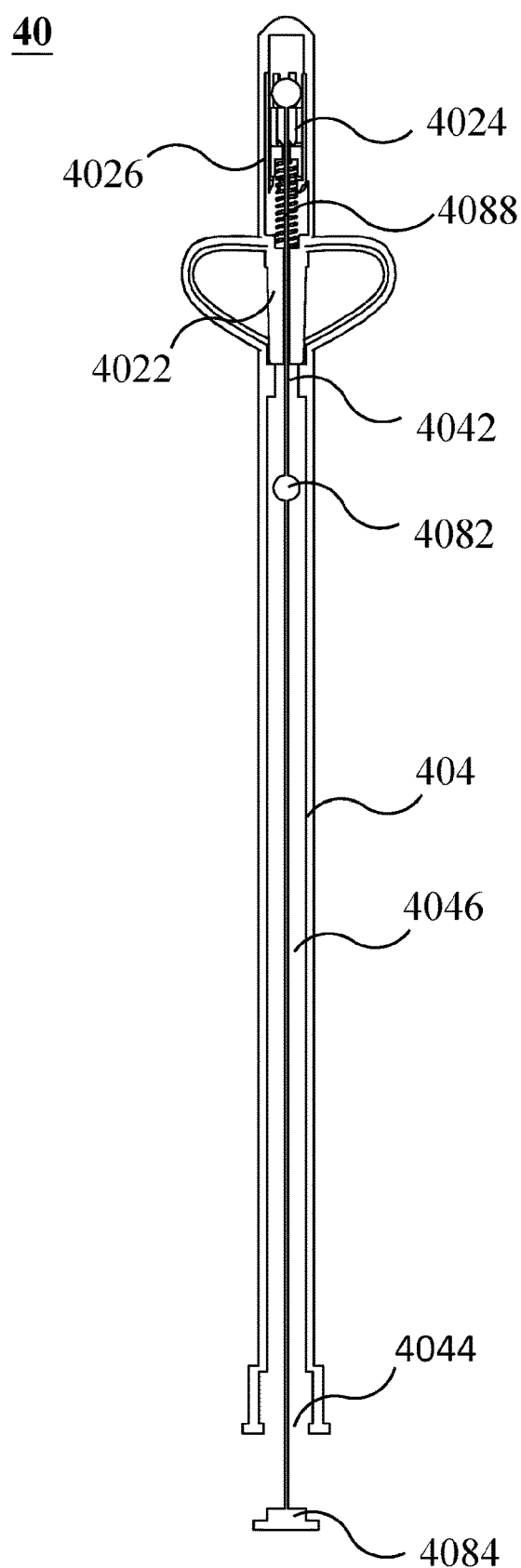

Furthermore, FIG. 6C illustrates the intermediate state of the catheter 40 between the tubular shape/state (as FIG. 6B shows) and the normal state (as FIG. 6A shows). As FIG. 6C shows, when the operator adjusts the second valve mechanism 4084 so as to move the cylindrical block 4022 to engage with the inlet 4042, the biasing element 4088 is compressed and the locking gear 4024 is moved to a third position relative to the teeth 4026. It is worth to know that the locking gear 4024 is not secured at the third position (as opposed to its first and second positions) by the teeth 4026. In other words, FIG. 6C intends to demonstrate the operation of the catheter 40 between when the locking gear 4024 is in the first position (as FIG. 6A shows) or the second position (as FIG. 6B shows). Particularly, in the FIG. 6C operation, an operator applies a force to the second valve mechanism 4084. Depending on its strating state, the catheter 40 either goes from FIG. 6A to 6C then to 6B, or from FIG. 6B to 6C and then 6A. The operation in FIG. 6C toggles the catheter 40 such that it becomes readily-removable (or not) from the subject's body. The foregoing is achieved by the restoring force of the biasing element 4088 in response to the operator releasing the second valve mechanism 4084 after applying force to it, as shown in FIG. 6C.

Note that the conventional catheter with elongated tube has the problem of urine retaining within the catheter. The dual valve mechanism and the locking module of the catheter 40 resolves such problem. As FIG. 6C shows, when the operator pulls the second valve mechanism 4084 and puts the catheter 40 in the intermediate state, the first valve mechanism 4082 and the second valve mechanism 4084 are respectively disengaged from the inlet 4042 and the outlet 4044, and the cylindrical block 4022 securely engages and blocks the inlet 4042. In other words, the inlet 4042 is closed but the outlet 4044 is open. Accordingly, the urine inside the passageway 4046 can be drained out completely. As a result, the issue of urine residue in the catheter itself may be better avoided.

Figure 6D:
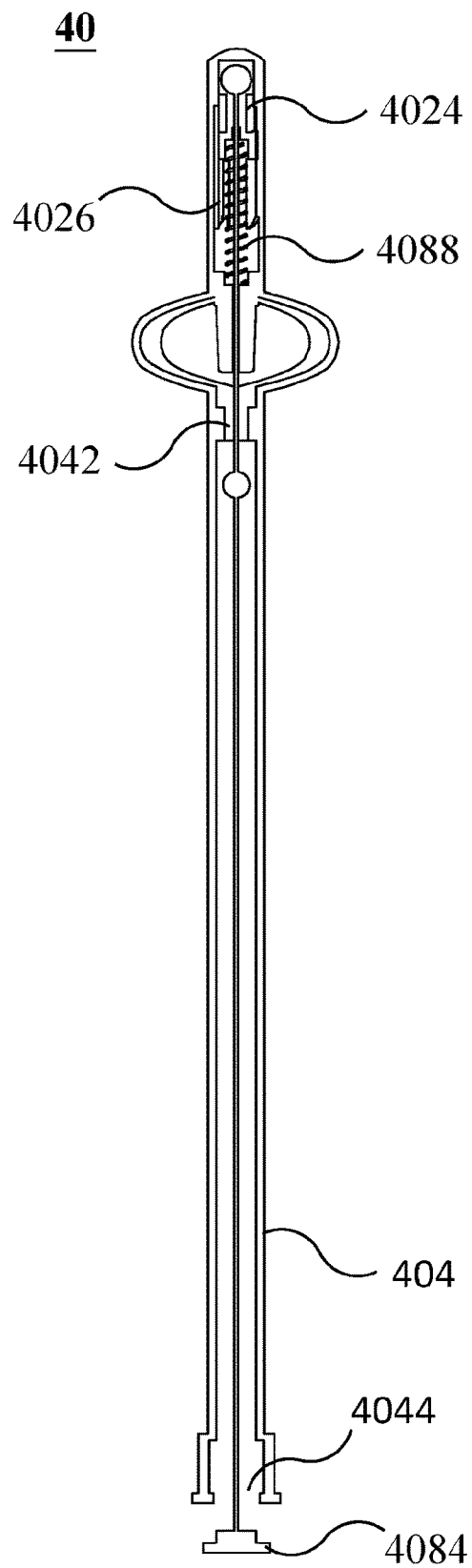

FIG. 6D illustrates a schematic diagram of using the catheter 40 to drain the body fluid (e.g., urine) inside the body cavity (e.g., bladder) when the catheter 40 is in the normal state/shape. As FIG. 6D shows, when the operator needs to drain the urine, he/she simply pulls out the second valve mechanism 4084 to slightly move the locking gear 4024 away from the first position but not to the third position and to compress the biasing element 4088. Hence, the inlet 4042 and the outlet 4044 are opened, and the body fluid is drained out through the second portion 404 of the catheter 40. Here, if the operator releases the second valve mechanism 4084, the catheter 40 will return to the normal state (as FIG. 6A shows) due to the restoring force of the biasing element 4088 (i.e., the locking gear 4024 being secured at the first position by the teeth 4026). In other words, the amount of force applied by the operator in FIG. 6D (for draining urine in the body cavity) is smaller than that in FIG. 6C (for draining urine residue in the catheter). The force applied in the operation of FIG. 6C needs to be substantial so as to switch the locking gear 4024 between first and second positions. On the other hand, the force applied in the operation of FIG. 6D is not meant to achieve the foregoing. That it, the operator only intends to drain the urine from the body cavity, as opposed to switch the catheter 40 to a state readily removable from the subject's body.

Furthermore, because the catheter 40 is an unembedded catheter, the preferable length of the second portion 404 of the catheter 40 is about 15-20 centimeters. To achieve the previous functions, the catheters of the present disclosure can be made from polyvinyl chloride (PVC), silicon, thermoplastic polyurethane (TPU), thermo-plastic-rubber (TPR) or any combination thereof.

LISTING OF ELEMENTS 10, 20, 30, 40 Catheter
50 Bladder
51 Urethra
52 Prostate
53 External urethral sphincter muscle
54 Spongy urethra
55 Urine
102, 202, 302, 402 First portion
104, 204, 404 Second portion
106, 206, 306, 406 Flexible portion
108, 208 Adjusting mechanism
112, 212 Extraction wire
210, 310 Controlling wire
1042, 2042, 3042, 4042 Inlet
1044, 2044, 4044 Outlet
1046, 2046, 4046 Passageway
1048, 2048, 3048 Sheath
1084, 2084 First end
1086 Second end
2082, 3082, 4082 First valve mechanism
3088, 4088 Biasing element
3090, 4090 Connecting wire
3092, 4092 Compartment
4022 Cylindrical block
4024 Locking gear
4026 Teeth
4084 Second valve mechanism

What is claimed is:

1. A catheter for guiding a body fluid of a subject, comprising:

an elongated body having a proximal tip, a distal tip and further including a first portion, a second portion and a flexible portion between the first and the second portions, the first portion and the second portion are co-axial, and the second portion includes a circumferential wall defining a passageway for the body liquid, the passageway further includes an inlet and an outlet; and an adjusting mechanism with opposing first and second ends, the first end engages the first portion and a first valve mechanism is configured at the second end, the first valve mechanism engages the second portion proximate to the inlet of the passageway, the body fluid can enter the passageway via the inlet when the first valve mechanism is retracted within the elongated body to open the passageway and the body fluid is blocked from entering the passageway when the first valve mechanism is not retracted and engages the first portion;

wherein the adjusting mechanism has a first, second and third state during use whereby in the first state the flexible portion expands to anchor the catheter inside the subject, in the second state the adjusting mechanism causes the flexible portion to contract to allow insertion or withdrawal of the catheter into/from the subject, and in a third state causes the flexible portion to expand beyond the expansion point of the first state and causes the first valve mechanism to open so the body fluid is directed to enter the passageway via the inlet of the second portion and exit via the outlet of the second portion.

2. The catheter according to claim 1, wherein the first portion of the elongated body further comprises a compartment and the adjusting mechanism further comprises a biasing element close to the first end, and the biasing element is received within the compartment.

3. The catheter according to claim 2, wherein the biasing element is compressed in the second state.

4. The catheter according to claim 1, wherein the adjusting mechanism is stretched in the second state.

5. The catheter according to claim 1, wherein the catheter further comprises an extraction wire connected to the second portion, said extraction wire is adapted to extend outside the subject such that it can be easily pulled to withdraw the catheter.

6. The catheter according to claim 1, wherein the first portion of the elongated body further comprises a compartment, and the adjusting mechanism further comprises a biasing element near the first end, wherein the biasing element is received within the compartment.

7. The catheter according to claim 1, wherein the adjusting mechanism comprises a controlling wire configured to open or close the first valve mechanism.

8. The catheter according to claim 7, wherein the flexible portion further expands such that the flexible portion and the first portion are more securely anchored within the subject when the controlling wire is pulled to open the first valve mechanism.

9. The catheter according to claim 7, wherein the catheter further comprises:
a locking module received within the first portion and engages with the adjusting mechanism; and
a second valve mechanism at a distal end of the controlling wire, wherein the second valve mechanism controls the body fluid from leaving the passageway via the outlet;
wherein the locking module controls the opening and closing of the inlet when the adjusting mechanism is not in the second state.

10. The catheter according to claim 9, wherein the outlet of the passageway is configured to be outside the subject.

11. The catheter according to claim 1, wherein the flexible portion comprises at least two arms.

12. The catheter according to claim 1, wherein a material of the catheter comprises polyvinyl chloride (PVC), silicon, thermoplastic polyurethane (TPU), thermoplastic-rubber (TPR) or any combination thereof.

13. The catheter according to claim 1, wherein only the first portion and the flexible portion are placed in a cavity of the subject when the catheter is not in the second state.

14. The catheter according to claim 1, wherein the cavity is defined by a bladder.

15. The catheter according to claim 2, wherein the biasing element is stretched in the second state.

16. The catheter according to claim 1, wherein said elongated body is substantially tubular shaped.

* * * * *